United States Patent
McLaren et al.

(10) Patent No.: US 10,899,695 B2
(45) Date of Patent: Jan. 26, 2021

(54) PROCESS FOR THE SYNTHESIS OF 1-ARYL-1-TRIFLUOROMETHYLCYCLO-PROPANES

(71) Applicant: IDORSIA PHARMACEUTICALS LTD, Allschwil (CH)

(72) Inventors: Lee McLaren, Runcorn (GB); Daniel To, Runcorn (GB); David Tovell, Lymm (GB); Stefan Abele, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 16/483,247

(22) PCT Filed: Feb. 5, 2018

(86) PCT No.: PCT/EP2018/052808
§ 371 (c)(1),
(2) Date: Aug. 2, 2019

(87) PCT Pub. No.: WO2018/141961
PCT Pub. Date: Aug. 9, 2018

(65) Prior Publication Data
US 2019/0375702 A1    Dec. 12, 2019

(30) Foreign Application Priority Data
Feb. 6, 2017 (EP) ...................... 17154826

(51) Int. Cl.
| | |
|---|---|
| *C07C 51/363* | (2006.01) |
| *C07C 67/343* | (2006.01) |
| *C07C 51/38* | (2006.01) |
| *C07C 57/58* | (2006.01) |
| *C07C 17/093* | (2006.01) |
| *C07C 57/62* | (2006.01) |
| *C07C 69/65* | (2006.01) |
| *C07C 51/09* | (2006.01) |

(52) U.S. Cl.
CPC .......... *C07C 51/363* (2013.01); *C07C 17/093* (2013.01); *C07C 51/38* (2013.01); *C07C 57/58* (2013.01); *C07C 57/62* (2013.01); *C07C 67/343* (2013.01); *C07C 51/09* (2013.01); *C07C 69/65* (2013.01); *C07C 2601/02* (2017.05)

(58) Field of Classification Search
CPC ....... C07C 67/343; C07C 69/65; C07C 51/09; C07C 51/38; C07C 51/363; C07C 57/58; C07C 57/62; C07C 17/093; C07C 2601/02
See application file for complete search history.

(56) References Cited

U.S. PATENT DOCUMENTS

| | | |
|---|---|---|
| 7,935,699 B2 | 5/2011 | Berthel et al. |
| 8,501,955 B2 | 8/2013 | Bhuniya et al. |
| 9,932,314 B2 | 4/2018 | Siegrist et al. |
| 10,065,929 B2 | 9/2018 | Siegrist et al. |
| 10,246,426 B2 | 4/2019 | Bezencon et al. |
| 2008/0146625 A1 | 6/2008 | Berthel et al. |
| 2009/0325987 A1 | 12/2009 | Muthuppalniappan et al. |
| 2010/0310493 A1 | 12/2010 | Bhuniya et al. |
| 2012/0289698 A1 | 11/2012 | Ashcraft et al. |
| 2013/0196964 A1* | 8/2013 | Harter .................. A61K 31/498 514/210.18 |
| 2015/0329533 A1 | 11/2015 | Nam et al. |
| 2016/0106102 A1 | 4/2016 | Kuebbeler et al. |
| 2017/0096399 A1* | 4/2017 | Siegrist ............... C07D 405/12 |
| 2018/0105496 A1 | 4/2018 | Siegrist et al. |
| 2018/0230109 A1 | 8/2018 | Bezencon et al. |

FOREIGN PATENT DOCUMENTS

| | | |
|---|---|---|
| EP | 2 402 327 | 1/2012 |
| EP | 2 530 078 | 12/2012 |
| WO | WO 96/00218 | 1/1996 |
| WO | WO 98/28269 | 7/1998 |
| WO | WO 02/00651 | 1/2002 |
| WO | WO 02/053101 | 7/2002 |
| WO | WO 02/053160 | 7/2002 |
| WO | WO 03/037274 | 5/2003 |
| WO | WO 03/051315 | 6/2003 |
| WO | WO 03/051833 | 6/2003 |
| WO | WO 03/101423 | 12/2003 |
| WO | WO 2004/089303 | 10/2004 |
| WO | WO 2004/089306 | 10/2004 |
| WO | WO 2004/099154 | 11/2004 |

(Continued)

OTHER PUBLICATIONS

U.S. Appl. No. 16/470,109, filed Jun. 14, 2019, Kessler et al.

(Continued)

*Primary Examiner* — Yate' K Cutliff
(74) *Attorney, Agent, or Firm* — Hoxie & Associates LLC

(57) ABSTRACT

The present invention relates to a process for the manufacturing of 1-aryl-1-trifluoromethylcyclopropanes, which serve as intermediates for the manufacturing of calcium T channel blockers of the general formula (A)

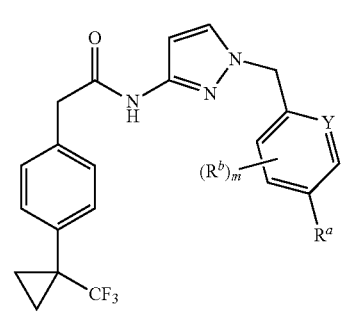

which are described in WO 2015/186056.

17 Claims, No Drawings

(56) References Cited

FOREIGN PATENT DOCUMENTS

| WO | WO 2005/056532 | 6/2005 | | |
|---|---|---|---|---|
| WO | WO 2006/018725 | 2/2006 | | |
| WO | WO 2006/066968 | 6/2006 | | |
| WO | WO 2006/114274 | 11/2006 | | |
| WO | WO 2006/114313 | 11/2006 | | |
| WO | WO 2007/073497 | 6/2007 | | |
| WO | WO 2007/120729 | 10/2007 | | |
| WO | WO 2008/012227 | 1/2008 | | |
| WO | WO 2008/085888 | 7/2008 | | |
| WO | WO 2008/156726 | 12/2008 | | |
| WO | WO 2009/054982 | 4/2009 | | |
| WO | WO 2009/054983 | 4/2009 | | |
| WO | WO 2009/054984 | 4/2009 | | |
| WO | WO 2009/118596 | 10/2009 | | |
| WO | WO 2009/121623 | 10/2009 | | |
| WO | WO 2010/073011 | 7/2010 | | |
| WO | WO 2010/075376 | 7/2010 | | |
| WO | WO 2010/122089 | 10/2010 | | |
| WO | WO 2010/139731 | 12/2010 | | |
| WO | WO 2011/022315 | 2/2011 | | |
| WO | WO 2011/042798 | 4/2011 | | |
| WO | WO 2011/053542 | 5/2011 | | |
| WO | WO 2011/084402 | 7/2011 | | |
| WO | WO 2012/027322 | 3/2012 | | |
| WO | WO 2012/077932 | 6/2012 | | |
| WO | WO 2012/120397 | 9/2012 | | |
| WO | WO 2013/011033 | 1/2013 | | |
| WO | WO 2013/134142 | 9/2013 | | |
| WO | WO 2014/125408 | 8/2014 | | |
| WO | WO 2014/179564 | 11/2014 | | |
| WO | WO 2014/187928 | 11/2014 | | |
| WO | WO2015/18605 | * | 12/2015 | ........... C07D 403/12 |
| WO | WO 2015/186056 | 12/2015 | | |
| WO | WO 2016/041892 | 3/2016 | | |
| WO | WO 2016/123533 | 8/2016 | | |
| WO | WO 2018/109152 | 6/2018 | | |
| WO | WO 2019/008034 | 1/2019 | | |

OTHER PUBLICATIONS

Anderson, M.P. et al., "Thalamic $Ca_v3.1$ T-type $Ca^{2+}$ channel plays a crucial role in stabilizing sleep," *PNAS*, 2005, vol. 102(5): 1743-1748.

Barnes-Seeman, D. et al., "Metabolically Stable tert-Butyl Replacement," *ACS Medicinal Chemistry Letters*, 2013, vol. 4: 514-516.

Becker, A.J. et al., "Transcriptional Upregulation of $Ca_v3.2$ Mediates Epileptogenesis in the Pilocarpine Model of Epilepsy," *The Journal of Neuroscience*, 2008, vol. 28(49): 13341-13353.

Benoff, S. et al., "The effect of calcium ion channel blockers on sperm fertilization potential," *Fertility and Sterility*, 1994, vol. 62(3): 606-617.

Berg, A.T. et al., "Revised terminology and concepts for organization of seizures and epilepsies: Report of the ILAE Commission on Classification and Terminology, 2005-2009," *Epilepsia*, 2010, vol. 51(4): 676-685.

Bhave, G. et al., "Posttranslational Mechanisms of Peripheral Sensitization," *J Neurobiol*, 2004, vol. 61: 88-106.

Bourinet, E. et al., "Silencing of the $Ca_v3.2$ T-type calcium channel gene in sensory neurons demonstrates its major role in nociception," *The EMBO Journal*, 2005, vol. 24(2): 315-324.

Broicher, T. et al., "Correlation of T-Channel Coding Gene Expression, $I_T$, and the Low Threshold $Ca^{2+}$ Spike in the Thalamus of a Rat Model of Absence Epilepsy," *Molecular and Cellular Neuroscience*, 2008, 66 pages.

Burmakov, A.I. et al., "Journal of Organic Chemistry of the USSR (English Translation)," *Russian Original*, 1972, vol. 8(1), Part 2, 4 pages.

Cavelier, P. et al., "Participation of low-threshold $Ca^{2+}$ spike in the Purkinje cells complex spike," *NeuroReport*, 2008, vol. 19(3): 299-303.

Cheong, E. et al., "T-type $Ca^{2+}$ channels in absence epilepsy," *Pflugers Arch—Eur J Physiol*, 2014, vol. 466: 719-734.

Cho, Y. et al., "The SAR analysis of TRPV1 agonists with the α-methylated B-region," *Bioorganic & Medicinal Chemistry Letters*, 2012, vol. 22: 5227-5231.

Coderre, T.J. et al., "Contribution of central neuroplasticity to pathological pain: review of clinical and experimental evidence," *Pain*, 1993, vol. 52: 259-285.

Destexhe, A. et al., "A Model of Spindle Rhythmicity in the Isolated Thalamic Reticular Nucleus," *Journal of Neurophysiology*, 1994, vol. 72(2): 803-818.

Dmowski, W. et al., "Selective reactions of 1,1-cycloalkanedicarboxylic acids with SF4. A route to 1,1-bis(trifluoromethyl)cycloalkanes,1-fluoroformyl-1-(trifluoromethyl)cycloalkanes and 1-(trifluoromethyl)-1-cycloalkanecarboxylic acids," *Journal of Fluorine Chemistry*, 2000, vol. 102: 141-146.

Dmowski, W. et al., "Reactions of Sulfur Tetrafluoride with Carboxylic Acids. Part 3. Reactions with Alkanecarboxylic, Cycloalkanecarboxylic and Certain Benzenecarboxylic Acids," *Roczniki Chemmi*, 1974, 1 page.

Dmowski, W. et al., "Reactions of Sulfur Tetrafluoride with Carboxylic Acids. Part V. The Role of Hydrogen Fluoride and the Mechanism of the Reactions," *Polish Journal of Chemistry*, 1978, vol. 52: 547-559.

Flatters, S.J.L. et al., "T-type calcium channels: a potential target for the treatment of chronic pain," *Drugs of the Future*, 2005, vol. 30(6): 573-580.

Giordanetto, F. et al., "T-type calcium channels inhibitors: a patent review," *Expert Opinion Ther. Patents*, 2011, vol. 21(1): 85-101.

Graef, J.D. et al., "An Acquired Channelopathy Involving Thalamic T-Type $Ca^{2+}$ Channels after Status Epilepticus," *The Journal of Neuroscience*, 2009, vol. 29(14): 4430-4441.

Greene, T.W. et al., "Protective Groups in Organic Synthesis," 3rd Edition, Wiley-Interscience, 1999, 3 pages.

Gutnick, M.J. et al., "Low threshold calcium spikes, intrinsic neuronal oscillation and rhythm generation in the CNS," *Journal of Neuroscience Methods*, 1989, vol. 28: 93-99.

Hall, A. et al., "Non-acidic pyrazole EP1 receptor antagonists with in vivo analgesic efficacy," *Bioorganic & Medicinal Chemistry Letters*, 2008, vol. 18: 3392-3399.

Hall, K.E. et al., "Voltage-dependent calcium currents are enhanced in dorsal root ganglion neurones from the Bio Bred/Worchester diabetic rat," *Journal of Physiology*, 1995, vol. 486(2): 313-322.

Hell, Z. et al., "Reaction of cyclopropane carboxylic acid derivatives with sulphur tetrafluoride—An example of a diastereoselective ring opening," *Journal of Fluorine Chemistry*, 2000, vol. 104: 297-301.

Heron, S.E. et al., "Extended Spectrum of Idiopathic Generalized Epilepsies Associated with CACNA1H Functional Variants," *Ann Neurol*, 2007, vol. 62(6): 560-568.

Huguenard, J.R. et al., "Intrathalamic Rhythmicity Studied in vitro: Nominal T-Current Modulation Causes Robust Antioscillatory Effects," *The Journal of Neuroscience*, 1994, vol. 14(9): 5485-5502.

Iftinca, M.C., "Neuronal T-type calcium channels: What's new?" *Journal of Medicine and Life*, 2011, vol. 4(2): 126-138.

Iftinca, M.C. et al., "Regulation of neuronal T-type calcium channels," *Trends in Pharmacological Sciences*, 2008, vol. 30(1): 32-40.

International Search Report of International Application No. PCT/IB2015/054164, dated Aug. 3, 2015, 3 pages.

Isabel, E. et al., "The discovery of MK-0674, an orally bioavailable cathepsin K inhibitor," *Bioorganic & Medicinal Chemistry Letters*, 2010, vol. 20: 887-892.

Jagodic, M.M. et al., "Upregulation of the T-Type Calcium Current in Small Rat Sensory Neurons After Chronic Constrictive Injury of the Sciatic Nerve," *J Neurophysiol*, 2008, vol. 99: 3151-3156.

Jagodic, M.M. et al., "Cell-Specific Alterations of T-Type Calcium Current in Painful Diabetic Neuropathy Enhance Excitability of Sensory Neurons," *The Journal of Neuroscience*, 2007, vol. 27(12): 3305-3316.

Jeanmonod, D. et al., "Low-threshold calcium spike bursts in the human thalamus. Common physiopathology for sensory, motor and limbic positive symptoms," *Brain*, 1996, vol. 119: 363-375.

(56) References Cited

OTHER PUBLICATIONS

Khosravani, H. et al., "Voltage-Gated Calcium Channels and Idiopathic Generalized Epilepsies," *Physiol Rev*, 2006, vol. 86: 941-966.
Kim, D. et al., "Lack of the Burst Firing of Thalamocortical Relay Neurons and Resistance to Absence Seizures in Mice Lacking $\beta_{1G}$ T-Type $Ca^{2+}$ Channels," *Neuron*, 2001, vol. 31: 35-45.
Kiss, L.E. et al., "Discovery of a Long-Acting, Peripherally Selective Inhibitor of Catechol-O-methyltransferase," *J. Med. Chem.*, 2010, vol. 53: 3396-3411.
Lambert, R.C. et al., "The many faces of T-type calcium channels," *Pflugers Arch—Eur J Physiol*, 2014, vol. 466: 415-423.
Latham, J.R. et al., "Selective T-Type Calcium Channel Blockade Alleviates Hyperalgesia in ob/ob Mice," *Diabetes*, 2009, vol. 58: 2656-2665.
Lee, J. et al., "Synthesis and anti-proliferative activity evaluation of N3-acyl-N5-aryl-3,5-diaminoindazole analogues as anti-head and neck cancer agent," *DARU Journal of Pharmaceutical Sciences*, 2014, vol. 22(4), 9 pages.
Lee, J. et al., "Lack of delta waves and sleep disturbances during non-rapid eye movement sleep in mice lacking $\alpha 1_G$-subunit of T-type calcium channels," *PNAS*, 2004, vol. 101(52): 18195-18199.
Llinás, R. et al., "Oscillatory Properties of Guinea-Pig Inferior Olivary Neurones and Their Pharmacological Modulation: An in Vitro Study," *J. Physiol.*, 1986, vol. 376: 163-182.
Lorentzen, R.J. et al., "Application of the Benzene Sector and the Benzene Chirality Rules to Perhydrobenzocycloalkenes and Related Compounds," *J. Am. Chem. Soc.*, 1992, vol. 114: 2181-2187.
Lory, P. et al., "Calcium channelopathies in inherited neurological disorders: Relevance to drug screening for acquired channel disorders," *IDRUGS*, 2010, vol. 13(7): 467-471.
McGivern, J.G., "Targeting N-type and T-type calcium channels for the treatment of pain," *Drug Discovery Today*, 2006, vol. 11(5/6): 245-253.
Mercadante, M.A. et al., "1,3-γ-Silyl-elimination in electron-deficient cationic systems," *Chemical Science*, 2014, vol. 5: 3983-3994.
Messinger, R.B. et al., "In vivo silencing of the $Ca_v3.2$ T-type calcium channels in sensory neurons alleviates hyperalgesia in rats with streptozocin-induced diabetic neuropathy," *Pain*, 2009, 12 pages.
Miwa, H. et al., "T-Type Calcium Channel as a New Therapeutic Target for Tremor," *Cerebellum*, 2011, vol. 10: 563-569.
Nelson, M.T. et al., "The Role of T-Type Calcium Channels in Epilepsy and Pain," *Current Pharmaceutical Design*, 2006, vol. 12(18): 2189-2197.
Pagé, D. et al., "Novel benzimidazole derivatives as selective CB2 agonists," *Bioorganic & Medicinal Chemistry Letters*, 2008, vol. 18:3695-3700.
Park, Y.G. et al., "$Ca_v3.1$ is a tremor rhythm pacemaker in the inferior olive," and Supplemental, *PNAS*, 2010, vol. 107(23): 12 pages.
Powell, K.L. et al., "A $Ca_v3.2$ T-Type Calcium Channel Point Mutation Has Splice-Variant-Specific Effects on Function and Segregates with Seizure Expression in a Polygenic Rat Model of Absence Epilepsy," *The Journal of Neuroscience*, 2009, vol. 29(2): 371-380.
Pustovit, Y.M. et al., "Reactions of cycloalkanecarboxylic acids with $SF_4$. I. Fluorination of cyclopropanepolycarboxylic acids with $SF_4$," *Journal of Fluorine Chemistry*, 1994, vol. 69: 225-229.
Reger, T.S. et al., "Pyridyl amides as potent inhibitors of T-type calcium channels," *Bioorganic & Medicinal Chemistry Letters*, 2011, vol. 21: 1692-1696.
Remington, The Science and Practice of Pharmacy, 21$^{st}$ Edition, 2005, Part 5, Pharmaceutical Manufacturing, 5 pages.

Song, I. et al., "Role of the α1G T-Type Calcium Channel in Spontaneous Absence Seizures in Mutant Mice," *The Journal of Neuroscience*, 2004, vol. 24(22): 5249-5257.
Stahl, P.H. et al., "Handbook of Pharmaceutical Salts. Properties, Selection and Use" *International Union of Pure and Applied Chemistry (IUPAC)*, 2008, pp. 330-350.
Steriade, M., "Sleep, epilepsy and thalamic reticular inhibitory neurons," *TRENDS in Neurosciences*, 2005, vol. 28(6): 317-324.
Su, H. et al., "Upregulation of a T-Type $Ca^{2+}$ Channel Causes a Long-Lasting Modification of Neuronal Firing Mode after Status Epilepticus," *The Journal of Neuroscience*, 2002, vol. 22(9): 3645-3655.
Talley, E.M. et al., "Differential Distribution of Three Members of a Gene Family Encoding Low Voltage-Activated (T-Type) Calcium Channels," *The Journal of Neuroscience*, 1999, vol. 19(6): 1895-1911.
Talley, E.M. et al., "Low-voltage-activated calcium channel subunit expression in a genetic model of absence epilepsy in the rat," *Molecular Brain Research*, 2000, vol. 75: 159-165.
Todorovic, S.M. et al., "T-type voltage-gated calcium channels as targets for the development of novel pain therapies," *British Journal of Pharmacology*, 2011, vol. 163: 484-495.
Todorovic, S.M. et al., "Regulation of T-Type Calcium Channels in the Peripheral Pain Pathway," *Channels*, 2007, vol. 1(4): 238-245.
Trofymchuk, S. et al., "A Facile Synthesis of Isomeric C-(2,2,2-Trifluoroethyl)anilines," *Synthesis*, 2012, vol. 44: 1974-1976.
Tsakiridou, E. et al., "Selective Increase in T-Type Calcium Conductance of Reticular Thalamic Neurons in a Rat Model of Absence Epilepsy," *The Journal of Neuroscience*, 1995, vol. 15(4): 3110-3117.
Uslaner, J.M. et al., "T-Type Calcium Channel Antagonism Decreases Motivation for Nicotine and Blocks Nicotine- and Cue-Induced Reinstatement for a Response Previously Reinforced with Nicotine," *Biol Psychiatry*, 2010, vol. 68:712-718.
Wang, X. et al., "Pd(II)-Catalyzed Hydroxyl-Directed C—H Activation/ C—O Cyclization: Expedient Construction of Dihydrobenzofurans," *J. Am. Chem. Soc.*, 2010, vol. 132(35): 12203-12205.
Wen, X.J. et al., "Intrathecal administration of $Ca_v3.2$ and $Ca_v3.3$ antisense oligonucleotide reverses tactile allodynia and thermal hyperalgesia in rats following chronic compression of dorsal root of ganglion," *Acta Pharmacologica Sinica*, 2006, vol. 27(12): 1547-1552.
Wildburger, N.C. et al., "Neuroprotective effects of blockers for T-type calcium channels," *Molecular Neurodegeneration*, 2009, vol. 4(44), 8 pages.
Woods, M., "SexRx: Calcium Channel Blockers and Your Sex Life," Accessed online Apr. 11, 2017, (http://www.winhosp.org/health-libraly/article?id=22043), 3 pages.
Wouters, J. et al., Pharmaceutical Salts and Co-crystals, *RSC Drug Discovery*, 2012, Chapters 1-16, 10 pages.
Xie, X. et al., "Validation of High Throughput Screening ASSAYS Against Three Subtypes of $Ca_v3$ T-Type Channels Using Molecular and Pharmacologic Approaches," *ASSAY and Drug Development Technologies*, 2007, vol. 5(2): 191-203.
Yaari, Y. et al., "Recruitment of apical dendritic T-type $Ca^{2+}$ channels by backpropagating spikes underlies de novo intrinsic bursting in hippocampal epileptogenesis," *J Physiol*, 2007, vol. 580(2): 435-450.
Yang, Y.C. et al., "The T-type calcium channel as a new therapeutic target for Parkinson's disease," *Pflugers Arch—Eur J Physiol*, 2014, vol. 466: 747-755.
Yang, Z.Q. et al., "Short-Acting T-Type Calcium Channel Antagonists Significantly Modify Sleep Architecture in Rodents," *ACS Medicinal Chemistry Letters*, 2010, vol. 1: 504-509.
Zamponi, G.W. et al., "Role of voltage-gated calcium channels in epilepsy," *Pflugers Arch—Eur J Physiol*, 2010, vol. 460: 395-403.

\* cited by examiner

PROCESS FOR THE SYNTHESIS OF 1-ARYL-1-TRIFLUOROMETHYLCYCLO-PROPANES

CROSS REFERENCE TO RELATED APPLICATIONS

This application is a United States Application under 35 U.S.C. 371 claiming benefit of PCT Application No. PCT/EP2018/052808, filed on Feb. 5, 2018, which claims the benefit of European Patent Application No. EP 17154826.6, filed on Feb. 6, 2017, the contents of each of which are incorporated herein by reference.

The present invention relates to a process for the manufacturing of 1-aryl-1-trifluoromethylcyclopropanes, which serve as intermediates for the manufacturing of calcium T channel blockers of the general formula (A)

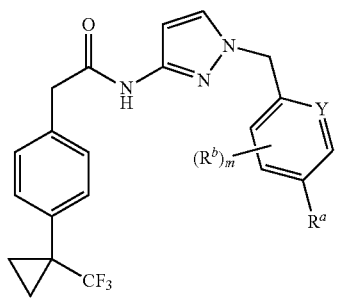

A which are described in WO 2015/186056.

The target molecule of the present invention is the phenylacetic acid of Formula (I)

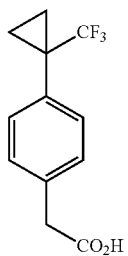

I

It is produced in WO 2015/186056 from the compound of formula (II) wherein $R^1$ is Br, by a Negishi coupling with the Rieke reagent (2-(tert-butoxy)-2-oxoethyl)zinc(II) chloride, followed by deprotection of the tert-butyl ester (see Scheme 1):

Scheme 1

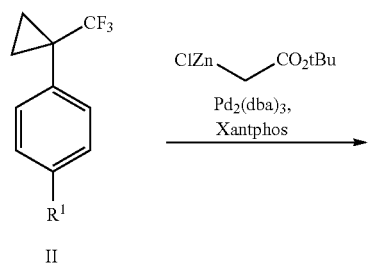

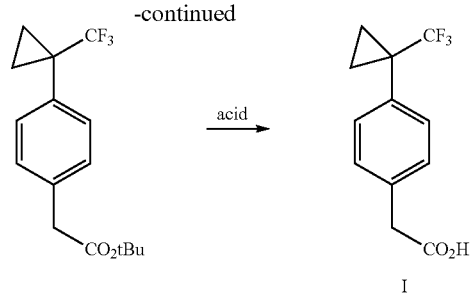

The problem of this process, however, is that it would be very difficult and expensive to scale up for the manufacturing of larger amounts.

It is therefore the object of the present invention to provide a process for the manufacture of the compound of formula (I) which overcomes the problems of the state of the art, i.e. a process which can be scaled up in order to prepare the desired product.

Several approaches for the synthesis of the compound of formula (I) are conceivable. Such approaches shall be described as routes 1, 2, 3 and 4 in Scheme 2. A common feature of all these approaches is the deoxotrifluorination of an appropriate carboxylic acid precursor (VIII), (X), (IIa) and (IIb), in order to obtain the desired trifluoromethyl group in the compounds of formula (IX), (XI), (IIIa) and (IIIb).

Scheme 2

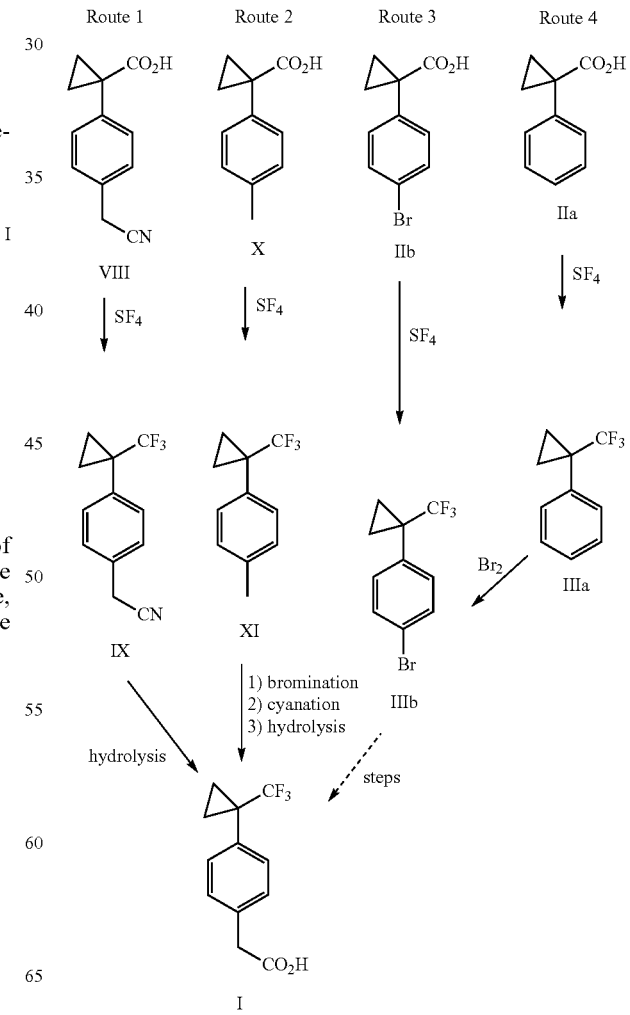

Starting material (VIII) can be synthesized by methods known to those skilled in the art, starting materials (X), (IIa) and (IIb) are commercially available. As these four substrates are only differing in the residue at the 4-position of the benzene ring (cyanomethyl, Me, Br, H), i.e. at a remote position from the carboxylic acid group (six C-atoms away), the artisan would not expect significant differences in selectivity or conversion when subjected to SF$_4$. Surprisingly, the differences turned out to be wide.

Substrates (VIII) and (X) did not give any desired product. Reaction of the cyanomethyl derivative (VIII) with SF$_4$ and HF in DCM gave mainly the acid fluoride, and forced reaction conditions like a tenfold increase of the HF load or prolonged reaction times at 100° C., only led to decomposition. Reaction of the methyl derivative (X) with SF$_4$ and HF in DCM only gave the acid fluoride, and forced conditions, like using HF as solvent or prolonged reaction time again only led to decomposition.

By contrast thereto, the bromo-derivative (IIb) gave 50% conversion to the desired trifluoromethyl product at mild conditions. When the reaction was run at 100° C. for 35 h, 85% conversion was observed. An unexpected increase in reactivity, selectivity, and conversion was observed when subjecting the H-derivative (IIa) to mild conditions of SF$_4$ and HF in dichloromethane. Full conversion was achieved with excellent selectivity (>90% GC purity) in favor of the product (IIIa).

Non-Obviousness of Conditions that Work Only for a Particularly Narrow Range of Phenyl-Sybstituted Cyclopropanecarboxylic Acid The high reactivity of the substrate (IIb) towards the deoxotrifluorination with SF$_4$ to compound (IIIb) is even more surprising when closely related bromo derivatives (IIc) and (IId) are compared. The only product isolated in both latter cases was the acid fluoride. When the reactions were run at higher temperature or in neat HF to convert the acid fluoride to the desired trifluoromethyl product, the acid fluoride was isolated together with decomposition products. A person skilled in the art would not have predicted such significant differences between those structurally similar substrates.

Scheme 3

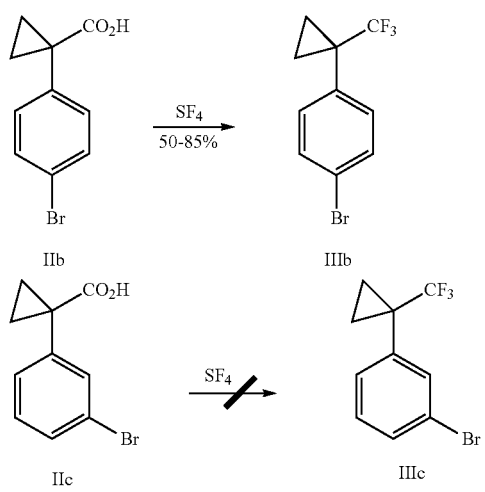

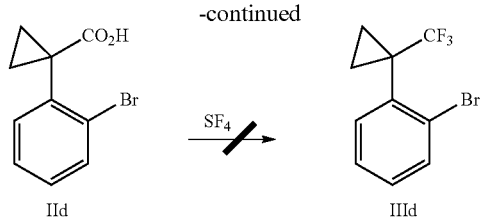

Surprising Selectivity and Reactivity Put into Perspectives with Prior Art for the Deoxotrifluorination of Cyclopropylcarboxylic Acids and Phenylacetic Acids The substrate (IIa) has both a) a phenylacetic acid and b) a cyclopropyl carboxylic acid moiety. Both phenylacetic acids and cyclopropylcarboxylic acids are notoriously difficult substrates for the SF$_4$-mediated deoxotrifluorination.

a) Surprisingly mild conditions. Phenylacetic acid was transformed into (2,2,2-trifluoroethyl)benzene with SF$_4$ in 55% yield (Dmowski et al., Roczniki Chemii 1974, 48, 1697). Higher yields of up to 90% were only realized with phenylacetic acids with an electron-withdrawing substituent in the 4-position, for example a nitro group (Trofymchuk et al. Synthesis 2012, 44, 1974-1976). More importantly, already a mono-alkylation of the α-carbon atom of phenylacetic acid, as for instance in indane-1-carboxylic acid, results in a yield of the deoxofluorination reaction of only 48% (Lorentzen et al. J. Am. Chem. Soc. 1992, 114, 2181, SF$_4$ in hexane, 70° C.); thus it would be expected that the yield for geminally dialkylated phenylacetic acids such as compound (IIa) is even lower. It is known that electron-donating groups (and groups that can be in conjugation with the fluorocarbonyl group in acyl fluorides, +M effect) de-activate the step from the acyl fluoride to the CF$_3$ group, see Dmowski et al., Roczniki Chemii 1974, 48, 1697 (p. 1702), Dmowski, Polish J. Chem. 1978, 52, 547 (p. 554-556), and Burmakov et al. J Org. Chem. USSR (Engl. Transl.) 1972, 8, 153-154.

It is therefore surprising to get full conversion with compound (IIa) and good conversion with compound (IIb) as compared to phenylacetic acid, using rather mild, i.e. diluted conditions.

b) Surprisingly mild conditions. Cyclopropanecarboxylic acid is a substrate that is notoriously very difficult to react with SF$_4$ (Dmowski et al., Roczniki Chemii 1974, 48, 1697): the yield was 6% with SF$_4$ (2.3-2.5 eq.) at 120° C. for 3 h, "cyclopropanecarboxylic acid exhibits a particularly low reactivity" (p. 1701). To get a higher yield (56%), HF (1.5 eq.) had to be added (Dmowski at al., Polish J. Chem. 1978, 52, 547).

Further examples showing the need for harsh conditions for the transformation of a cyclopropylcarboxylic acid into the CF$_3$ derivative:

a) Hell et al., J. Fluorine Chem. 2000, 104, 297-301: 1-(ethoxycarbonyl)cyclopropane-1-carboxylic acid required neat SF$_4$ at 60° C. for 21 h. Even under these drastic conditions, an approximately 1:1 mixture of the intermediate acid fluoride and the desired CF$_3$ product was obtained. Applying milder conditions for other geminally disubstituted cyclopropane carboxlic acids only gave the acid fluoride.

b) Pustovit et al. J. Fluorine Chem. 1994, 69, 225-229: trans-cyclopropane-1,2-dicarboxylic acid reacted in neat SF$_4$ (8 eq.) at 125° C. for 5 h in moderate yield (48%).

c) Dmowski et al. J. Fluorine Chem. 2000, 102, 141-146: 1,1-cyclopropanedicarboxylic acid required neat SF$_4$ (6 eq.) at 120° C. for 24 h for full conversion with a moderate yield (59%).

In the following the present invention will be described and various embodiments of the invention are presented.

1) In a first embodiment, the present invention relates to a process for the manufacturing of the compound of formula (I)

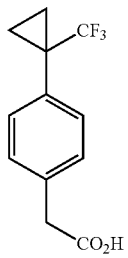

I said process comprising the reaction of a compound of formula (II)

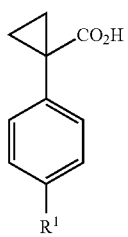

II wherein R¹ is H or Br,
with SF₄ and HF, to give a compound of formula (III)

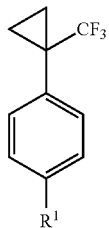

III wherein R¹ is H or Br.

2) In one embodiment of the invention according to 1), R¹ is H.
3) In one embodiment of the invention according to 1), R¹ is Br.
4) In one embodiment according to 1) to 3), the reaction of the compound of formula (II) is done in a solvent selected from dichloromethane, dichloroethane, chloroform, and toluene. The amount of solvent is from 1 to 15 vol.
5) In one embodiment, the solvent used in any one of 1) to 4) is dichloromethane.
6) In a further embodiment according to any one of 1) to 5), the amount of SF₄ is 2 to 10 equivalents in relation to starting material compound (II). Lower limits of SF₄ are 2.0, 2.3, 2.5, 2.7, 2.8, and 2.9 equivalents, upper limits are 10, 9, 8, 7, 6, 5, 4 and 3.5 equivalents. It is to be understood that each lower limit can be combined with each upper limit. Hence all combinations shall herewith be disclosed. A preferred amount of SF₄ is from 2.8 to 3.5 equivalents, particularly preferred are 2.9 to 3.2 equivalents, for example 3 equivalents.
7) In one embodiment according to any one of 1), or 4) to 6), R¹ is H, and the amount of HF is from 0.4 to 2.5 equivalents. Lower limits of HF are 0.4, 0.45, 0.5 and 0.8 equivalents. Upper limits are 1.2, 1.5, 1.7, 2.0 and 2.5 equivalents. It is to be understood that each lower limit can be combined with each upper limit. Hence all combinations shall herewith be disclosed. A preferred amount of HF is from 0.5 to 1.5 equivalents, more preferred are 0.8 to 1.2 equivalents, for example 1 equivalent.

These limits are based on experiments, which have been applied in the reaction of compound (IIa) with SF₄ and in dichloromethane as solvent. At first, the reaction was performed with 2.4 equivalents of HF which gave crude material with impurities that required three distillations to afford the desired compound in sufficient purity. In further experiments the amount of HF was reduced in a range of 0.45 to 1.03 equivalents (table 1). It appears that the various amounts of HF gave product of similar purity, but the isolated yields were reduced with lower amounts of HF. This is probably due to lower conversion of the starting material over the course of the reaction time, which was 16 h in each case. However, on each occasion, the desired product was isolated with the need of only one distillation relative to the three distillations when 2.4 equivalents of HF had been used.

Table 1 shows a summary of fluorination reactions on compound (IIa) in DCM (1 vol), anhydrous HF, SF₄ (3.0 eq.), 75° C., 16 h.

TABLE 1

| reaction | HF amount | HF eq. | yield (g)[a], (%) |
|---|---|---|---|
| 1 | 170 mL | 0.45 | 1847, 54% |
| 2 | 200 mL | 0.54 | 2018, 59% |
| 3 | 300 mL | 0.81 | 2409, 70% |
| 4 | 400 mL | 1.03 | 2678, 78% |

[a]After distillation.

8) In one embodiment according to any one of 1), or 4) to 6), R¹ is Br and the amount of HF is from 1.5 to 2.5 equivalents. Lower limits of HF are 1.5, 1.7, and 1.9 equivalents. Upper limits are 2.5, 2.3, and 2.1 equivalents. It is to be understood that each lower limit can be combined with each upper limit, hence all combinations shall herewith be disclosed. A preferred amount of HF is from 1.7 to 2.3 equivalents, more preferred are 1.9 to 2.1 equivalents, for example 2 equivalents.
9) In one embodiment according to any one of 1) or 4) to 7), R¹ is H and the reaction temperature for the deoxotrifluorination is from 65° C. to 85° C., preferably from 70° C. to 80° C., more preferably from 73° C. to 77° C., for example around 75° C., wherein the reaction is done in a closed container.
10) In one embodiment according to any one of 1), 4) to 6) or 8), R¹ is Br and the reaction temperature for the deoxotrifluorination is from 65° C. to 110° C., preferably from 90° C. to 110° C., for example around 100° C., wherein the reaction is done in a closed container.
11) Reaction times are typically in the range of 11 to 40 hours. In case R¹ is H, the reaction time is preferably from 11 to 21 hours, for example around 16 hours. In case R¹ is Br, the reaction time is preferably from 30 to 40 hours, for example around 35 hours.

12) A further embodiment of the invention relates to a process according to any one of 1) to 11), said process further comprising the reaction of a compound of formula (III)

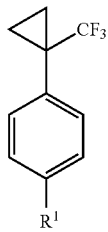

wherein R¹ is Br, with

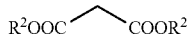

to give a compound of formula (V)

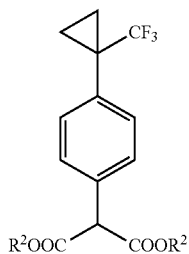

wherein R² is methyl, ethyl, isopropyl, n-butyl or benzyl.

Besides the dialkylmalonate (IV), the reaction requires a solvent, K₃PO₄, Pd(OAc)₂ and (2-biphenyl)di-tert-butylphosphine (also known as JohnPhos) or other phosphine ligands. The dialkylmalonate, preferably the dimethylmalonate, is added in slight excess compared to compound (III) (1 equivalent), i.e. the dialkylmalonate is added in an amount of 1.01 to 1.1 equivalents, preferably 1.03 to 1.07 equivalents, for example 1.05 equivalents. K₃PO₄ is added in 2 to 5 equivalents. Lower limits of K₃PO₄ are 2.0, 2.3, 2.5, and 2.7 equivalents. Upper limits are 5.0, 4.5, 4.0, 3.5 and 3.2 equivalents. It is to be understood that each lower limit can be combined with each upper limit, hence all combinations shall herewith be disclosed. Preferably about 3 equivalents are used. Pd(OAc)₂ is added in catalytic amounts, i.e. in 0.01 to 0.1 equivalents, preferably 0.01 to 0.06 equivalents, for example 0.03 equivalents. (2-Biphenyl)di-tert-butylphosphine is added in the amount of 0.02 to 0.2 equivalents, preferably 0.02 to 0.12 equivalents, for example in 0.06 equivalents. The solvent can be toluene, dioxane, acetonitrile and others with a similar boiling point, preferred is toluene.

13) In one embodiment according to 12), R² is methyl.

14) In one embodiment of the invention, compound (V) can be isolated.

15) In one embodiment of the invention, compound (V) is used in the next step without further isolation and/or purification, but used as such, in the organic solvent of the preceeding reaction.

The process for the transformation of compound (IIIb) to compound (I) is depicted in Scheme 4 for the preferred case that R² is methyl:

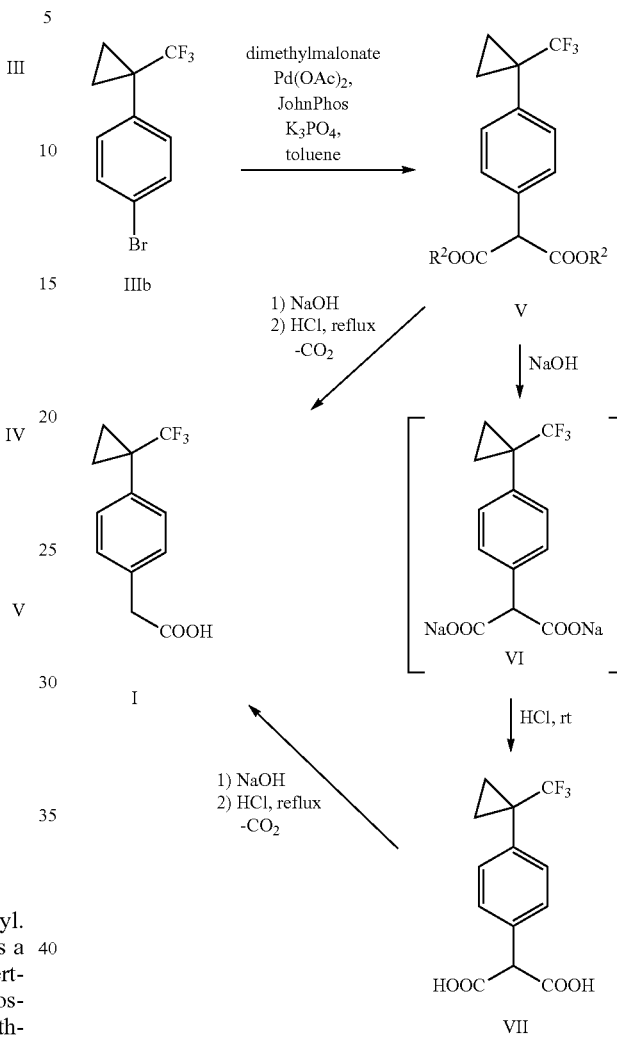

16) A further embodiment of the invention relates to a process according to any one of 12) to 15), said process further comprising one of the following steps a orb:

a) treatment of the compound of formula (V)

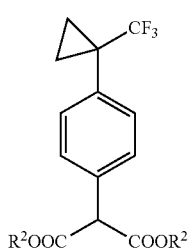

wherein R² is methyl, ethyl, isopropyl, n-butyl or benzyl (preferably methyl), a1) with NaOH solution, followed by a2) treatment with HCl at 75-100° C.; or b) treatment of the compound of formula (V), wherein $R^2$ is methyl, ethyl, isopropyl, n-butyl, or benzyl (preferably methyl),
  b1) with NaOH solution, followed by treatment with HCl at 15-30° C. to obtain an intermediate product of formula (VII)

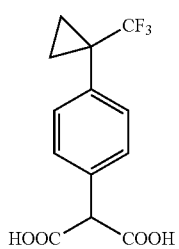

b2) followed by decarboxylation with HCl at 75-100° C. to obtain the product of formula (I)

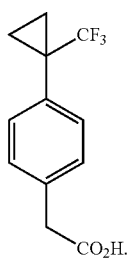

In order to obtain the desired compound (I), the present invention comprises two alternatives.

17) The first alternative of 16) uses a one-pot hydrolysis-decarboxylation reaction. Thereby, compound (V) (1 equivalent) in an organic solvent such as toluene, chlorobenzene, heptane or dichloromethane, preferably toluene, is subjected to an excess of NaOH, preferably 32% aqueous NaOH solution. Alternatively, other bases are possible as well, for instance KOH or LiOH. Preferably, NaOH is used in in an amount of 2-5 eq., preferably 3.5 eq. The hydrolysis reaction is carried out at reflux temperature, i.e. at about 100 to 105° C. when toluene is used as organic solvent.

After termination of the hydrolysis, the product is collected in the water phase, which has a basic pH value, for example pH 14. Preferably, co-evaporation with toluene is applied, before the decarboxylation step is started.

Decarboxylation is performed with an aqueous acid such as HCl or $H_2SO_4$, preferably HCl, more preferably 32% HCl. The water phase is kept acidic, and the product compound (I) is collected in the organic phase and dried.

18) According to the second alternative of 16), the intermediate acid compound (VII) is isolated, before it is subjected to decarboxylation. In a first step, compound (V), dissolved in an organic solvent such as toluene, chlorobenzene, heptane or dichloromethane, preferably in toluene, and subjected to water and a base, preferably NaOH, preferably 32% aqueous NaOH solution. The base is taken in an amount of 2-5 eq., preferably 3.5 eq. After hydrolysis, the acid VII is precipitated by addition of an acid, preferably HCl, preferably 32% HCl, at 15-30° C.; the pH of the aqueous phase is set to pH 1-2.

In a second step, the compound (VII) is subjected to decarboxylation by dissolving compound (VII) in water and NaOH, preferably 32% NaOH, followed by decarboxylation in acidic azeotropic medium, preferably comprising 20% HCl, in order to afford the desired product compound (I).

19) A further embodiment of the invention relates to a process for the manufacturing of the compound of formula (III)

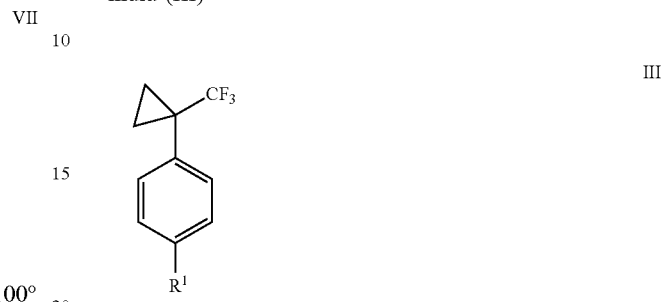

said process comprising the reaction of a compound of formula (II)

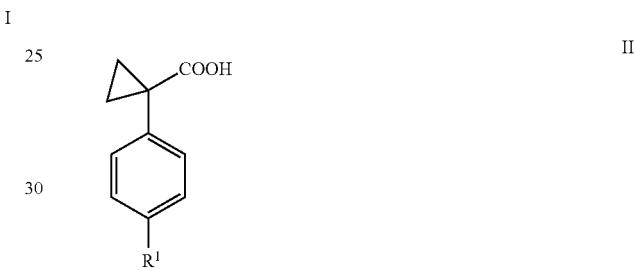

wherein $R^1$ is H or Br, with $SF_4$ and HF.

Preferably, further conditions are chosen from any one of embodiments 4) to 11), excluding embodiment 1).

20) A further embodiment of the invention relates to the process according to 19), wherein dichloromethane is used as a solvent.

21) A further embodiment of the invention relates to the process according to embodiment 19) or 20), wherein $SF_4$ is added in an amount of 2.7 to 10 equivalents, preferably in an amount of 2.8 to 3.5 equivalents.

22) A further embodiment of the invention relates to the process according to any one of embodiments 19) to 21), wherein $R^1$ is H, and the amount of HF is from 0.4 to 2.5 equivalents, preferably from 0.5 to 1.5 equivalents.

23) A further embodiment of the invention relates to the process according to any one of embodiments 19) to 21), wherein $R^1$ is Br, and the amount of HF is from 1.5 to 2.5 equivalents, preferably from 1.7 to 2.3 equivalents.

24) A further embodiment of the invention relates to a compound of formula (Va)

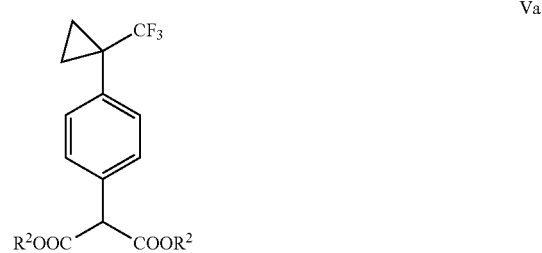

wherein R² is methyl, ethyl, isopropyl, n-butyl, benzyl, or H, or a salt of said compound.

25) A further embodiment of the invention relates to a compound of formula (Va) according to embodiment 24), wherein R² is H.

26) A further embodiment of the invention relates to the use of the compound of formula (Va) according to any one of embodiments 24) or 25), or a salt thereof, in a process for manufacturing the compound of formula (I) as defined in 1), or a salt thereof. The salts are selected from a Li-, Na-, K-, Mg-, Ca-, or a NR₄⁺-salt, wherein R represents independently of each other H or $(C_{1-4})$alkyl.

The term "alkyl", used alone or in combination, refers to a saturated straight or branched chain hydrocarbon group containing one to four carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of $(C_{1-4})$alkyl groups are methyl, ethyl, n-propyl, isopropyl, n-butyl, sec.-butyl, tert.-butyl, and isobutyl. Preferred are methyl and ethyl. Most preferred is methyl.

This invention thus notably relates to the manufacturing processes, the compounds and uses as defined in one of embodiments 1), 19), 24) and 26) or to these manufacturing processes, compounds and uses further limited under consideration of their respective dependencies by the characteristics of any one of embodiments 2) to 18), 20) to 23) and 25). In particular, based on the dependencies of the different embodiments as disclosed hereinabove, the following manufacturing process, compound and use embodiments are thus possible and intended and herewith specifically disclosed in individualized form:

1, 2+1, 3+1, 4+1, 4+2+1, 4+3+1, 5+4+1, 5+4+2+1, 5+4+3+1, 6+1, 6+2+1, 6+3+1, 6+4+1, 6+4+2+1, 6+4+3+1, 6+5+4+1, 6+5+4+2+1, 6+5+4+3+1, 7+1, 7+4+1, 7+4+2+1, 7+4+3+1, 7+5+4+1, 7+5+4+2+1, 7+5+4+3+1, 7+6+1, 7+6+2+1, 7+6+3+1, 7+6+4+1, 7+6+4+2+1, 7+6+4+3+1, 7+6+5+4+1, 7+6+5+4+2+1, 7+6+5+4+3+1, 8+1, 8+4+1, 8+4+2+1, 8+4+3+1, 8+5+4+1, 8+5+4+2+1, 8+5+4+3+1, 8+6+1, 8+6+2+1, 8+6+3+1, 8+6+4+1, 8+6+4+2+1, 8+6+4+3+1, 8+6+5+4+1, 8+6+5+4+2+1, 8+6+5+4+3+1, 9+7+1, 9+7+4+1, 9+7+4+2+1, 9+7+4+3+1, 9+7+5+4+1, 9+7+5+4+2+1, 9+7+5+4+3+1, 9+7+6+1, 9+7+6+2+1, 9+7+6+3+1, 9+7+6+4+1, 9+7+6+4+2+1, 9+7+6+4+3+1, 9+7+6+5+4+1, 9+7+6+5+4+2+1, 9+7+6+5+4+3+1, 10+8+1, 10+8+4+1, 10+8+4+2+1, 10+8+4+3+1, 10+8+5+4+1, 10+8+5+4+2+1, 10+8+5+4+3+1, 10+8+6+1, 10+8+6+2+1, 10+8+6+3+1, 10+8+6+4+1, 10+8+6+4+2+1, 10+8+6+4+3+1, 10+8+6+5+4+1, 10+8+6+5+4+2+1, 10+8+6+5+4+3+1, 11+1, 12+1, 12+2+1, 12+3+1, 12+4+1, 12+4+2+1, 12+4+3+1, 12+5+4+1, 12+5+4+2+1, 12+5+4+3+1, 12+6+1, 12+6+2+1, 12+6+3+1, 12+6+4+1, 12+6+4+2+1, 12+6+4+3+1, 12+6+5+4+1, 12+6+5+4+2+1, 12+6+5+4+3+1, 12+7+1, 12+7+4+1, 12+7+4+2+1, 12+7+4+3+1, 12+7+5+4+1, 12+7+5+4+2+1, 12+7+5+4+3+1, 12+7+6+1, 12+7+6+2+1, 12+7+6+3+1, 12+7+6+4+1, 12+7+6+4+2+1, 12+7+6+4+3+1, 12+7+6+5+4+1, 12+7+6+5+4+2+1, 12+7+6+5+4+3+1, 12+8+1, 12+8+4+1, 12+8+4+2+1, 12+8+4+3+1, 12+8+5+4+1, 12+8+5+4+2+1, 12+8+5+4+3+1, 12+8+6+1, 12+8+6+2+1, 12+8+6+3+1, 12+8+6+4+1, 12+8+6+4+2+1, 12+8+6+4+3+1, 12+8+6+5+4+1, 12+8+6+5+4+2+1, 12+8+6+5+4+3+1, 12+9+7+1, 12+9+7+4+1, 12+9+7+4+2+1, 12+9+7+4+3+1, 12+9+7+5+4+1, 12+9+7+5+4+2+1, 12+9+7+5+4+3+1, 12+9+7+6+1, 12+9+7+6+2+1, 12+9+7+6+3+1, 12+9+7+6+4+1, 12+9+7+6+4+2+1, 12+9+7+6+4+3+1, 12+9+7+6+5+4+1, 12+9+7+6+5+4+2+1, 12+9+7+6+5+4+3+1, 12+10+8+1, 12+10+8+4+1, 12+10+8+4+2+1, 12+10+8+4+3+1, 12+10+8+5+4+1, 12+10+8+5+4+2+1, 12+10+8+5+4+3+1, 12+10+8+6+1, 12+10+8+6+2+1, 12+10+8+6+3+1, 12+10+8+6+4+1, 12+10+8+6+4+2+1, 12+10+8+6+5+4+1, 12+10+8+6+5+4+2+1, 12+10+8+6+5+4+3+1, 12+11+1, 13+12+1, 13+12+2+1, 13+12+3+1, 13+12+4+1, 13+12+4+2+1, 13+12+4+3+1, 13+12+5+4+1, 13+12+5+4+2+1, 13+12+5+4+3+1, 13+12+6+1, 13+12+6+2+1, 13+12+6+3+1, 13+12+6+4+1, 13+12+6+4+2+1, 13+12+6+4+3+1, 13+12+6+5+4+1, 13+12+6+5+4+2+1, 13+12+6+5+4+3+1, 13+12+7+1, 13+12+7+4+1, 13+12+7+4+2+1, 13+12+7+4+3+1, 13+12+7+5+4+1, 13+12+7+5+4+2+1, 13+12+7+5+4+3+1, 13+12+7+6+1, 13+12+7+6+2+1, 13+12+7+6+3+1, 13+12+7+6+4+1, 13+12+7+6+4+2+1, 13+12+7+6+4+3+1, 13+12+7+6+5+4+1, 13+12+7+6+5+4+2+1, 13+12+7+6+5+4+3+1, 13+12+8+1, 13+12+8+4+1, 13+12+8+4+2+1, 13+12+8+4+3+1, 13+12+8+5+4+1, 13+12+8+5+4+2+1, 13+12+8+5+4+3+1, 13+12+8+6+1, 13+12+8+6+2+1, 13+12+8+6+3+1, 13+12+8+6+4+1, 13+12+8+6+4+2+1, 13+12+8+6+4+3+1, 13+12+8+6+5+4+1, 13+12+8+6+5+4+2+1, 13+12+8+6+5+4+3+1, 13+12+9+7+1, 13+12+9+7+4+1, 13+12+9+7+4+2+1, 13+12+9+7+4+3+1, 13+12+9+7+5+4+1, 13+12+9+7+5+4+2+1, 13+12+9+7+5+4+3+1, 13+12+9+7+6+1, 13+12+9+7+6+2+1, 13+12+9+7+6+3+1, 13+12+9+7+6+4+1, 13+12+9+7+6+4+2+1, 13+12+9+7+6+4+3+1, 13+12+9+7+6+5+4+1, 13+12+9+7+6+5+4+2+1, 13+12+9+7+6+5+4+3+1, 13+12+10+8+1, 13+12+10+8+4+1, 13+12+10+8+4+2+1, 13+12+10+8+4+3+1, 13+12+10+8+5+4+1, 13+12+10+8+5+4+2+1, 13+12+10+8+5+4+3+1, 13+12+10+8+6+1, 13+12+10+8+6+2+1, 13+12+10+8+6+3+1, 13+12+10+8+6+4+1, 13+12+10+8+6+4+2+1, 13+12+10+8+6+4+3+1, 13+12+10+8+6+5+4+1, 13+12+10+8+6+5+4+2+1, 13+12+10+8+6+5+4+3+1, 13+12+11+1, 16+12+1, 16+12+2+1, 16+12+3+1, 16+12+4+1, 16+12+4+2+1, 16+12+4+3+1, 16+12+5+4+1, 16+12+5+4+2+1, 16+12+5+4+3+1, 16+12+6+1, 16+12+6+2+1, 16+12+6+3+1, 16+12+6+4+1, 16+12+6+4+2+1, 16+12+6+4+3+1, 16+12+6+5+4+1, 16+12+6+5+4+2+1, 16+12+6+5+4+3+1, 16+12+7+1, 16+12+7+4+1, 16+12+7+4+2+1, 16+12+7+4+3+1, 16+12+7+5+4+1, 16+12+7+5+4+2+1, 16+12+7+5+4+3+1, 16+12+7+6+1, 16+12+7+6+2+1, 16+12+7+6+3+1, 16+12+7+6+4+1, 16+12+7+6+4+2+1, 16+12+7+6+4+3+1, 16+12+7+6+5+4+1, 16+12+7+6+5+4+2+1, 16+12+7+6+5+4+3+1, 16+12+8+1, 16+12+8+4+1, 16+12+8+4+2+1, 16+12+8+4+3+1, 16+12+8+5+4+1, 16+12+8+5+4+2+1, 16+12+8+5+4+3+1, 16+12+8+6+1, 16+12+8+6+2+1, 16+12+8+6+3+1, 16+12+8+6+4+1, 16+12+8+6+4+2+1, 16+12+8+6+4+3+1, 16+12+8+6+5+4+1, 16+12+8+6+5+4+2+1, 16+12+8+6+5+4+3+1, 16+12+9+7+1, 16+12+9+7+4+1, 16+12+9+7+4+2+1, 16+12+9+7+4+3+1, 16+12+9+7+5+4+1, 16+12+9+7+5+4+2+1, 16+12+9+7+5+4+3+1, 16+12+9+7+6+1, 16+12+9+7+6+2+1, 16+12+9+7+6+3+1, 16+12+9+7+6+4+1, 16+12+9+7+6+4+2+1, 16+12+9+7+6+4+3+1, 16+12+9+7+6+5+4+1, 16+12+9+7+6+5+4+2+1, 16+12+9+7+6+5+4+3+1, 16+12+10+8+1, 16+12+10+8+4+1, 16+12+10+8+4+2+1, 16+12+10+8+4+3+1, 16+12+10+8+5+4+1, 16+12+10+8+5+4+2+1, 16+12+10+8+5+4+3+1, 16+12+10+8+6+1, 16+12+10+8+6+2+1, 16+12+10+8+6+3+1, 16+12+10+8+6+4+1, 16+12+10+8+6+4+2+1, 16+12+10+8+6+4+3+1, 16+12+10+8+6+5+4+1, 16+12+10+8+6+5+4+2+1, 16+12+10+8+6+5+4+3+1, 16+12+11+1, 16+13+12+1, 16+13+12+2+1, 16+13+12+3+1, 16+13+12+4+1, 16+13+12+4+2+1, 16+13+12+4+3+1, 16+13+12+5+4+1, 16+13+12+5+4+2+1, 16+13+12+5+4+3+1, 16+13+12+6+1, 16+13+12+6+2+1, 16+13+12+6+3+1, 16+13+12+6+4+1, 16+13+12+6+4+2+1, 16+13+12+6+4+3+1, 16+13+12+6+5+4+1, 16+13+12+6+5+4+2+1, 16+13+12+6+5+4+3+1, 16+13+12+7+1, 16+13+12+7+4+1, 16+13+12+7+4+2+1, 16+13+12+7+4+3+1, 16+13+12+7+

5+4+1, 16+13+12+7+5+4+2+1, 16+13+12+7+5+4+3+1, 16+13+12+7+6+1, 16+13+12+7+6+2+1, 16+13+12+7+6+3+1, 16+13+12+7+6+4+1, 16+13+12+7+6+4+2+1, 16+13+12+7+6+4+3+1, 16+13+12+7+6+5+4+1, 16+13+12+7+6+5+4+2+1, 16+13+12+7+6+5+4+3+1, 16+13+12+8+1, 16+13+12+8+4+1, 16+13+12+8+4+2+1, 16+13+12+8+4+3+1, 16+13+12+8+5+4+1, 16+13+12+8+5+4+2+1, 16+13+12+8+5+4+3+1, 16+13+12+8+6+1, 16+13+12+8+6+2+1, 16+13+12+8+6+3+1, 16+13+12+8+6+4+1, 16+13+12+8+6+4+2+1, 16+13+12+8+6+4+3+1, 16+13+12+8+6+5+4+1, 16+13+12+8+6+5+4+2+1, 16+13+12+8+6+5+4+3+1, 16+13+12+9+7+1, 16+13+12+9+7+4+1, 16+13+12+9+7+4+2+1, 16+13+12+9+7+4+3+1, 16+13+12+9+7+5+4+1, 16+13+12+9+7+5+4+2+1, 16+13+12+9+7+5+4+3+1, 16+13+12+9+7+6+1, 16+13+12+9+7+6+2+1, 16+13+12+9+7+6+3+1, 16+13+12+9+7+6+4+1, 16+13+12+9+7+6+4+2+1, 16+13+12+9+7+6+4+3+1, 16+13+12+9+7+6+5+4+1, 16+13+12+9+7+6+5+4+2+1, 16+13+12+9+7+6+5+4+3+1, 16+13+12+10+8+1, 16+13+12+10+8+4+1, 16+13+12+10+8+4+2+1, 16+13+12+10+8+4+3+1, 16+13+12+10+8+5+4+1, 16+13+12+10+8+5+4+2+1, 16+13+12+10+8+5+4+3+1, 16+13+12+10+8+6+1, 16+13+12+10+8+6+2+1, 16+13+12+10+8+6+3+1, 16+13+12+10+8+6+4+1, 16+13+12+10+8+6+4+2+1, 16+13+12+10+8+6+4+3+1, 16+13+12+10+8+6+5+4+1, 16+13+12+10+8+6+5+4+2+1, 16+13+12+10+8+6+5+4+3+1, 16+13+12+11+1, 17+16+12+1, 17+16+12+2+1, 17+16+12+3+1, 17+16+12+4+1, 17+16+12+4+2+1, 17+16+12+4+3+1, 17+16+12+5+4+1, 17+16+12+5+4+2+1, 17+16+12+5+4+3+1, 17+16+12+6+1, 17+16+12+6+2+1, 17+16+12+6+3+1, 17+16+12+6+4+1, 17+16+12+6+4+2+1, 17+16+12+6+4+3+1, 17+16+12+6+5+4+1, 17+16+12+6+5+4+2+1, 17+16+12+6+5+4+3+1, 17+16+12+7+1, 17+16+12+7+4+1, 17+16+12+7+4+2+1, 17+16+12+7+4+3+1, 17+16+12+7+5+4+1, 17+16+12+7+5+4+2+1, 17+16+12+7+5+4+3+1, 17+16+12+7+6+1, 17+16+12+7+6+2+1, 17+16+12+7+6+3+1, 17+16+12+7+6+4+1, 17+16+12+7+6+4+2+1, 17+16+12+7+6+4+3+1, 17+16+12+7+6+5+4+1, 17+16+12+7+6+5+4+2+1, 17+16+12+7+6+5+4+3+1, 17+16+12+8+1, 17+16+12+8+4+1, 17+16+12+8+4+2+1, 17+16+12+8+4+3+1, 17+16+12+8+5+4+1, 17+16+12+8+5+4+2+1, 17+16+12+8+5+4+3+1, 17+16+12+8+6+1, 17+16+12+8+6+2+1, 17+16+12+8+6+3+1, 17+16+12+8+6+4+1, 17+16+12+8+6+4+2+1, 17+16+12+8+6+4+3+1, 17+16+12+8+6+5+4+1, 17+16+12+8+6+5+4+2+1, 17+16+12+8+6+5+4+3+1, 17+16+12+9+7+1, 17+16+12+9+7+4+1, 17+16+12+9+7+4+2+1, 17+16+12+9+7+4+3+1, 17+16+12+9+7+5+4+1, 17+16+12+9+7+5+4+2+1, 17+16+12+9+7+5+4+3+1, 17+16+12+9+7+6+1, 17+16+12+9+7+6+2+1, 17+16+12+9+7+6+3+1, 17+16+12+9+7+6+4+1, 17+16+12+9+7+6+4+2+1, 17+16+12+9+7+6+4+3+1, 17+16+12+9+7+6+5+4+1, 17+16+12+9+7+6+5+4+2+1, 17+16+12+9+7+6+5+4+3+1, 17+16+12+10+8+1, 17+16+12+10+8+4+1, 17+16+12+10+8+4+2+1, 17+16+12+10+8+4+3+1, 17+16+12+10+8+5+4+1, 17+16+12+10+8+5+4+2+1, 17+16+12+10+8+5+4+3+1, 17+16+12+10+8+6+1, 17+16+12+10+8+6+2+1, 17+16+12+10+8+6+3+1, 17+16+12+10+8+6+4+1, 17+16+12+10+8+6+4+2+1, 17+16+12+10+8+6+4+3+1, 17+16+12+10+8+6+5+4+1, 17+16+12+10+8+6+5+4+2+1, 17+16+12+10+8+6+5+4+3+1, 17+16+12+11+1, 17+16+13+12+1, 17+16+13+12+2+1, 17+16+13+12+3+1, 17+16+13+12+4+1, 17+16+13+12+4+2+1, 17+16+13+12+4+3+1, 17+16+13+12+5+4+1, 17+16+13+12+5+4+2+1, 17+16+13+12+5+4+3+1, 17+16+13+12+6+1, 17+16+13+12+6+2+1, 17+16+13+12+6+3+1, 17+16+13+12+6+4+1, 17+16+13+12+6+4+2+1, 17+16+13+12+6+4+3+1, 17+16+13+12+6+5+4+1, 17+16+13+12+6+5+4+2+1, 17+16+13+12+6+5+4+3+1, 17+16+13+12+7+1, 17+16+13+12+7+4+1, 17+16+13+12+7+4+2+1, 17+16+13+12+7+4+3+1, 17+16+13+12+7+5+4+1, 17+16+13+12+7+5+4+2+1, 17+16+13+12+7+5+4+3+1, 17+16+13+12+7+6+1, 17+16+13+12+7+6+2+1, 17+16+13+12+7+6+3+1, 17+16+13+12+7+6+4+1, 17+16+13+12+7+6+4+2+1, 17+16+13+12+7+6+4+3+1, 17+16+13+12+7+6+5+4+1, 17+16+13+12+7+6+5+4+2+1, 17+16+13+12+7+6+5+4+3+1, 17+16+13+12+8+1, 17+16+13+12+8+4+1, 17+16+13+12+8+4+2+1, 17+16+13+12+8+4+3+1, 17+16+13+12+8+5+4+1, 17+16+13+12+8+5+4+2+1, 17+16+13+12+8+5+4+3+1, 17+16+13+12+8+6+1, 17+16+13+12+8+6+2+1, 17+16+13+12+8+6+3+1, 17+16+13+12+8+6+4+1, 17+16+13+12+8+6+4+2+1, 17+16+13+12+8+6+4+3+1, 17+16+13+12+8+6+5+4+1, 17+16+13+12+8+6+5+4+2+1, 17+16+13+12+8+6+5+4+3+1, 17+16+13+12+9+7+1, 17+16+13+12+9+7+4+1, 17+16+13+12+9+7+4+2+1, 17+16+13+12+9+7+4+3+1, 17+16+13+12+9+7+5+4+1, 17+16+13+12+9+7+5+4+2+1, 17+16+13+12+9+7+5+4+3+1, 17+16+13+12+9+7+6+1, 17+16+13+12+9+7+6+2+1, 17+16+13+12+9+7+6+3+1, 17+16+13+12+9+7+6+4+1, 17+16+13+12+9+7+6+4+2+1, 17+16+13+12+9+7+6+4+3+1, 17+16+13+12+9+7+6+5+4+1, 17+16+13+12+9+7+6+5+4+2+1, 17+16+13+12+9+7+6+5+4+3+1, 17+16+13+12+10+8+1, 17+16+13+12+10+8+4+1, 17+16+13+12+10+8+4+2+1, 17+16+13+12+10+8+4+3+1, 17+16+13+12+10+8+5+4+1, 17+16+13+12+10+8+5+4+2+1, 17+16+13+12+10+8+5+4+3+1, 17+16+13+12+10+8+6+1, 17+16+13+12+10+8+6+2+1, 17+16+13+12+10+8+6+3+1, 17+16+13+12+10+8+6+4+1, 17+16+13+12+10+8+6+4+2+1, 17+16+13+12+10+8+6+4+3+1, 17+16+13+12+10+8+6+5+4+1, 17+16+13+12+10+8+6+5+4+2+1, 17+16+13+12+10+8+6+5+4+3+1, 17+16+13+12+11+1, 18+16+12+1, 18+16+12+2+1, 18+16+12+3+1, 18+16+12+4+1, 18+16+12+4+2+1, 18+16+12+4+3+1, 18+16+12+5+4+1, 18+16+12+5+4+2+1, 18+16+12+5+4+3+1, 18+16+12+6+1, 18+16+12+6+2+1, 18+16+12+6+3+1, 18+16+12+6+4+1, 18+16+12+6+4+2+1, 18+16+12+6+4+3+1, 18+16+12+6+5+4+1, 18+16+12+6+5+4+2+1, 18+16+12+6+5+4+3+1, 18+16+12+7+1, 18+16+12+7+4+1, 18+16+12+7+4+2+1, 18+16+12+7+4+3+1, 18+16+12+7+5+4+1, 18+16+12+7+5+4+2+1, 18+16+12+7+5+4+3+1, 18+16+12+7+6+1, 18+16+12+7+6+2+1, 18+16+12+7+6+3+1, 18+16+12+7+6+4+1, 18+16+12+7+6+4+2+1, 18+16+12+7+6+4+3+1, 18+16+12+7+6+5+4+1, 18+16+12+7+6+5+4+2+1, 18+16+12+7+6+5+4+3+1, 18+16+12+8+1, 18+16+12+8+4+1, 18+16+12+8+4+2+1, 18+16+12+8+4+3+1, 18+16+12+8+5+4+1, 18+16+12+8+5+4+2+1, 18+16+12+8+5+4+3+1, 18+16+12+8+6+1, 18+16+12+8+6+2+1, 18+16+12+8+6+3+1, 18+16+12+8+6+4+1, 18+16+12+8+6+4+2+1, 18+16+12+8+6+4+3+1, 18+16+12+8+6+5+4+1, 18+16+12+8+6+5+4+2+1, 18+16+12+8+6+5+4+3+1, 18+16+12+9+7+1, 18+16+12+9+7+4+1, 18+16+12+9+7+4+2+1, 18+16+12+9+7+4+3+1, 18+16+12+9+7+5+4+1, 18+16+12+9+7+5+4+2+1, 18+16+12+9+7+5+4+3+1, 18+16+12+9+7+6+1, 18+16+12+9+7+6+2+1, 18+16+12+9+7+6+3+1, 18+16+12+9+7+6+4+1, 18+16+12+9+7+6+4+2+1, 18+16+12+9+7+6+4+3+1, 18+16+12+9+7+6+5+4+1, 18+16+12+9+7+6+5+4+2+1, 18+16+12+9+7+6+5+4+3+1, 18+16+12+10+8+1, 18+16+12+10+8+4+1, 18+16+12+10+8+4+2+1, 18+16+12+10+8+4+3+1, 18+16+12+10+8+5+4+1, 18+16+12+10+8+5+4+2+1, 18+16+12+10+8+5+4+3+1, 18+16+12+10+8+6+1, 18+16+12+10+8+6+2+1, 18+16+12+10+8+6+3+1, 18+16+12+10+8+6+4+1, 18+16+12+10+8+6+4+2+1, 18+16+12+10+8+6+4+3+1, 18+16+12+10+8+6+5+4+1, 18+16+12+10+8+6+5+4+2+1, 18+16+12+10+8+6+5+4+3+1, 18+16+12+11+1, 18+16+13+12+1, 18+16+13+12+2+1, 18+16+13+12+3+1, 18+16+13+12+4+1, 18+16+13+12+4+2+1, 18+16+13+12+4+3+1, 18+16+13+12+5+4+1, 18+16+13+12+5+4+2+1, 18+16+

13+12+5+4+3+1, 18+16+13+12+6+1, 18+16+13+12+6+2+1, 18+16+13+12+6+3+1, 18+16+13+12+6+4+1, 18+16+13+12+6+4+2+1, 18+16+13+12+6+4+3+1, 18+16+13+12+6+5+4+1, 18+16+13+12+6+5+4+2+1, 18+16+13+12+6+5+4+3+1, 18+16+13+12+7+1, 18+16+13+12+7+4+1, 18+16+13+12+7+4+2+1, 18+16+13+12+7+4+3+1, 18+16+13+12+7+5+4+1, 18+16+13+12+7+5+4+2+1, 18+16+13+12+7+5+4+3+1, 18+16+13+12+7+6+1, 18+16+13+12+7+6+2+1, 18+16+13+12+7+6+3+1, 18+16+13+12+7+6+4+1, 18+16+13+12+7+6+4+2+1, 18+16+13+12+7+6+4+3+1, 18+16+13+12+7+6+5+4+1, 18+16+13+12+7+6+5+4+2+1, 18+16+13+12+7+6+5+4+3+1, 18+16+13+12+8+1, 18+16+13+12+8+4+1, 18+16+13+12+8+4+2+1, 18+16+13+12+8+4+3+1, 18+16+13+12+8+5+4+1, 18+16+13+12+8+5+4+2+1, 18+16+13+12+8+5+4+3+1, 18+16+13+12+8+6+1, 18+16+13+12+8+6+2+1, 18+16+13+12+8+6+3+1, 18+16+13+12+8+6+4+1, 18+16+13+12+8+6+4+2+1, 18+16+13+12+8+6+4+3+1, 18+16+13+12+8+6+5+4+1, 18+16+13+12+8+6+5+4+2+1, 18+16+13+12+8+6+5+4+3+1, 18+16+13+12+9+7+1, 18+16+13+12+9+7+4+1, 18+16+13+12+9+7+4+2+1, 18+16+13+12+9+7+4+3+1, 18+16+13+12+9+7+5+4+1, 18+16+13+12+9+7+5+4+2+1, 18+16+13+12+9+7+5+4+3+1, 18+16+13+12+9+7+6+1, 18+16+13+12+9+7+6+2+1, 18+16+13+12+9+7+6+3+1, 18+16+13+12+9+7+6+4+1, 18+16+13+12+9+7+6+4+3+1, 18+16+13+12+9+7+6+4+2+1, 18+16+13+12+9+7+6+5+4+1, 18+16+13+12+9+7+6+5+4+2+1, 18+16+13+12+9+7+6+5+4+3+1, 18+16+13+12+10+8+1, 18+16+13+12+10+8+4+1, 18+16+13+12+10+8+4+2+1, 18+16+13+12+10+8+4+3+1, 18+16+13+12+10+8+5+4+1, 18+16+13+12+10+8+5+4+2+1, 18+16+13+12+10+8+5+4+3+1, 18+16+13+12+10+8+6+1, 18+16+13+12+10+8+6+2+1, 18+16+13+12+10+8+6+3+1, 18+16+13+12+10+8+6+4+1, 18+16+13+12+10+8+6+4+2+1, 18+16+13+12+10+8+6+4+3+1, 18+16+13+12+10+8+6+5+4+1, 18+16+13+12+10+8+6+5+4+2+1, 18+16+13+12+10+8+6+5+4+3+1, 18+16+13+12+11+1, 19, 20+19, 21+19, 21+20+19, 22+19, 22+20+19, 22+21+19, 22+21+20+19, 23+19, 23+20+19, 23+21+19, 23+21+20+19, 24, 25+24, 26;

in the list above, the numbers refer to the embodiments according to their numbering provided hereinabove whereas "+" indicates the dependency from another embodiment. The different individualised embodiments are separated by commas. In other words, "4+2+1" for example refers to embodiment 4) depending on embodiment 2), depending on embodiment 1), i.e. embodiment "4+2+1" corresponds to embodiment 1) further limited by the features of embodiments 2) and 4).

ABBREVIATIONS AND TERMS USED IN THIS TEXT

Abbreviations

The following abbreviations are used throughout the specification and the examples:
Ac acetyl
aq aqueous
bp boiling point
DCM dichloromethane
eq. equivalent(s)
ET external temperature
GC gas chromatography
h hour(s)
IPC in process control
IT internal temperature
JohnPhos (2-biphenyl)di-tert-butylphosphine
LC-MS liquid chromatography—mass spectroscopy
min minute(s)
MS mass spectroscopy
MTBE tert.-butyl-methylether
NMR nuclear magnetic resonance
org. organic
rpm rounds per minute
rt room temperature
% a/a percent determined by area ratio
TFA trifluoroacetic acid
vol 1 vol means 1 L solvent per 1 kg reference starting material
wt 1 wt means 1 kg of reagent per 1 kg of reference starting material
LC-MS method
Column: Waters XBridge C18, 4.6×30 mm, 2.5 μm
Wavelength: 210 nm
Make up eluent: acetonitrile/water 7:3, 0.240 mL/min
Injection volume: 1.00 μL
Flow: 4.5 mL/min
Eluent A: water 0.04% TFA
Eluent B: acetonitrile
Gradient: 0.00-0.01 min: 5% B, 1.00-1.45 min: 95% B, 1.55-1.60 min: 5% B

EXPERIMENTAL PART

1. 1-(trifluoromethyl)cyclopropyl)benzene IIIa

1-Phenyl-1-cyclopropane carboxylic acid (1.0 eq.) (commercially available, Acros, No. 17068) was loaded into a 15 L stainless steel autoclave. A mixture of dichloromethane (1 vol) and anhydrous hydrogen fluoride (1 eq.) was prepared in a 5 L polypropylene bottle and transferred to the autoclave. $SF_4$ (3.0 eq.) was pressurized into the vessel and heated to 75° C. for 16 h. When cooled, the volatiles were vented through a concentrated potassium hydroxide scrubber and the contents transferred into a 20 L vessel of ice. The vessel was washed out with pressurized dichloromethane (0.5 vol). The solution was then carefully basified with a solution of 50% potassium hydroxide (5 vol) maintaining temperature below 25° C. The mixture was separated and the aqueous layer extracted with dichloromethane (2×1 vol). The combined organic layers were dried ($MgSO_4$) filtered, and concentrated at 50° C. under atmospheric pressure to give crude material as a brown liquid containing 36% dichloromethane (by 1H NMR spectra). The product was purified by distillation at bp 78-80° C. at 30 mmHg to give the desired product in 78% yield. $^1$H NMR (300 MHz, $CDCl_3$) δ: 0.01-1.15 (m, 2H), 1.33-1.56 (m, 2H), 7.28-7.79 (m, 5H); $^{19}$F NMR (300 MHz) δ: 3.05.

2. 1-bromo-4-(1-(trifluoromethyl)cyclopropyl)benzene IIIb 1-(4-Bromo-phenyl)cyclopropane carboxylic acid (1 eq.) (commercially available, Matrix Scientific, No. 82869) was placed in an autoclave. A mixture of anhydrous HF (2 eq.) and dichloromethane (2 vol) was added, followed by $SF_4$ (3 eq.). The vessel was then heated to 100° C. for 35 h. The reaction was cooled to rt, the volatiles were allowed to vest through a hydroxide scrubber and the vessel contents were transferred to a 5 L vessel of ice (1 vol) and washed with dichloromethane (0.5 vol). The solution was carefully basified with a solution of potassium hydrogen carbonate. Once the solution reached pH 8, the mixture was separated and the aqueous layer extracted with dichloromethane (2×1 vol). The combined organic layers were dried ($MgSO_4$) filtered and concentrated at atmospheric pressure. The crude product was purified by distillation at 85° C. at 1 mmHg to give the desired product (58%, >95% assay by 1H NMR and GC) as a pale yellow liquid. Analytical data correspond to those published (ACS Medicinal Chemistry Letters, 2013, 4, 514-516). $^1$H NMR (500 MHz, CDCl$_3$) δ: 1.01-1.05 (m, 2H), 1.36-1.41 (m, 2H), 7.33-7.39 (m, 2H), 7.48-7.51 (m, 2H)

3. 1-methyl-4-(1-(trifluoromethyl)cyclopropyl)benzene XI 1-(p-tolyl)cyclopropane carboxylic acid (1 eq.) (commercially available, Acros, No. 17070) was placed in an autoclave. A mixture of anhydrous HF (2 eq.) and dichloromethane (2 vol) was added, followed by SF$_4$ (3 eq.). The vessel was then heated to 100° C. for 72 h. The reaction was cooled to rt, the volatiles were allowed to vest through a hydroxide scrubber and the vessel contents were transferred to a 5 L vessel of ice (1 vol) and washed with dichloromethane (0.5 vol). Significant quantity of black tar was observed. The mixture was carefully basified with a solution of potassium hydrogen carbonate. Once the solution reached pH 8 the mixture was separated and the aqueous layer extracted with dichloromethane (2×1 vol). The combined organic layers were dried (MgSO$_4$), filtered and distilled at atmospheric pressure. 1H and 19F NMR showed no desired product, mainly decomposition products.

4. 2-(4-(1-(trifluoromethyl)cyclopropyl)phenyl)acetonitrile IX 1-(4-(cyanomethyl)phenyl)cyclopropane-1-carboxylic acid (VIII) was prepared from 1-(p-tolyl)cyclopropane carboxylic acid by methods known to those skilled in the art.

A solution of 1-(4-(cyanomethyl)phenyl)cyclopropane-1-carboxylic acid (VIII) (20 g, 1 eq.) and dichloromethane (1 vol) was stirred and anhydrous HF (2 eq.) was added. The 250 ml autoclave was evacuated and the solution was transferred to the autoclave under vacuum. SF$_4$ (3 eq.) was added under nitrogen pressure and the reaction was heated to 75° C. for 16 h. The reaction was cooled to rt, transferred to a 5 L vessel of ice (1 vol) and washed with dichloromethane (0.5 vol). The mixture was carefully basified with a solution of potassium hydrogen carbonate. Once the solution reached pH 8 the mixture was separated and the aqueous layer extracted with dichloromethane (2×1 vol). The combined organic layers were dried (MgSO$_4$), filtered and concentrated at atmospheric pressure to give a tarry material. $^1$H and $^{19}$F NMR showed no desired product, mainly acid fluoride.

5. 1-bromo-3-(1-(trifluoromethyl)cyclopropyl)benzene IIIc

5.1 1-(3-bromo-phenyl)cyclopropane-1-carbonitrile

3-Bromophenylacetonitrile (1 eq.), 1-bromo-2-chloroethane (1.5 eq.) and benzyl triethylammonium chloride (0.08 eq.) were placed into a 5 L 3-neck round bottom flask and stirred for 15 min. A solution of 50% aq sodium hydroxide (6 eq.) was added over 30 min. The reaction was heated at 60° C. for 16 h. IPC showed 100% completion. The reaction was cooled to rt and water (3.3 vol) and CH$_2$Cl$_2$ (3.3 vol) were added and layers separated. The aqueous layer was further extracted with CH$_2$Cl$_2$ (3.3 vol) and combined organics washed with water (3.3 vol), 1M HCl (3.3 vol) and brine (3.3 vol). The organic layer was dried (MgSO$_4$), filtered and concentrated under reduced pressure. The crude product was purified by distillation to give clean product (95-97%). $^1$H NMR (300 MHz, CDCl$_3$) δ: 1.36-1.51 (m, 2H), 1.70-1.85 (m, 2H), 7.22-7.29 (m, 2H), 7.41-7.48 (m, 2H).

5.2 1-(3-Bromo-phenyl)cyclopropane-1-carboxylic Acid 1-(3-bromo-phenyl)cyclopropane-1-carbonitrile (1 eq.), lithium hydroxide (2 eq.) and water (6.0 vol) was placed into a 5 L 3-neck round bottom flask. The reaction was heated at reflux (110° C.) for 16 h. The reaction was cooled to rt and diluted with water (5 vol). The aqueous was washed with CH$_2$Cl$_2$ (2×3 vol) and then the aqueous was acidified to pH 3 using concentrated HCl (~1 vol). This was then extracted with MTBE (2×3 vol), dried (MgSO$_4$), filtered and concentrated under reduced pressure to give a white crystalline powder (~92%). $^1$H NMR (300 MHz, CDCl$_3$) δ: 1.21-1.35 (m, 2H), 1.62-1.76 (m, 2H), 7.17-7.22 (m, 1H), 7.28-7.31 (m, 1H), 7.40-7.47 (m, 1H), 7.51-7.52 (m, 1H).

5.3 1-bromo-3-(1-(trifluoromethyl)cyclopropyl)benzene IIIc 1-(3-Bromo-phenyl)cyclopropane-1-carboxylic acid (1 eq.) was placed in an autoclave. To this was added dichloromethane (2 vol), anhydrous HF (2 eq.) followed by SF$_4$ (3 eq.). The vessel was then heated to 100° C. for 36 h. The reaction was cooled to rt, transferred to a 5 L vessel of ice (1 vol) and washed with dichloromethane (0.5 vol). The solution was carefully basified with a solution of potassium hydrogen carbonate. Once the solution reached pH 8, the mixture was separated and the aqueous layer was extracted with dichloromethane (2×1 vol). The combined organic layers were dried (MgSO$_4$), filtered and concentrated at atmospheric pressure to yield a mixture of acid fluoride and decomposition products.

6. 1-bromo-2-(1-(trifluoromethyl)cyclopropyl)benzene IIId 1-(2-Bromo-phenyl)cyclopropane carboxylic acid acid (1 eq.) (commercially available, Combi-Blocks) was placed in an autoclave and to this was added dichloromethane (2 vol), anhydrous HF (2 eq.), followed by SF$_4$ (3 eq.). The vessel was then heated to 100° C. for 36 h. The reaction was cooled to rt, transferred to a 5 L vessel of ice (1 vol) and washed with dichloromethane (0.5 vol). The solution was carefully basified with a solution of potassium hydrogen carbonate. Once the solution reached pH 8 the mixture was separated and the aqueous layer extracted with dichloromethane (2×1 vol). The combined organic layers were dried (MgSO$_4$), filtered and concentrated at atmospheric pressure to yield the acid fluoride.

7. 1-bromo-4-(1-(trifluoromethyl)cyclopropyl)benzene IIIb

The preparation has been performed in analogy to US2013/0196964 A1 [1340-1342].

7.1 Preparation of the Catalyst

To a 5 L 3-neck flask was charged a solution of zinc bromide (0.05 eq.) in anhydrous methanol (0.85 vol), K10 montmorillonite (0.24 vol) was added with stirring at rt under an atmosphere of nitrogen. The mixture was stirred at rt for 1 h. The solvent was removed under reduced pressure and the flask was connected to a distillation set up. Residual methanol was removed by heating to 200° C. under gentle vacuum (~450 mmHg) overnight to give a pink/beige fine solid (ca. 205 g). The catalyst was stored in a glass jar for use as required.

7.2 Bromination

To a 20 L flange flask was charged 1-phenyl-1-(trifluoromethyl)cyclopropane (1.0 eq.), pentane (6 vol) and the 'activated zinc bromide catalyst' (prepared above, 0.3 vol). The flask was then completely covered to reduce incidence of light and bromine (2.0 eq.) was added dropwise over 15 min at rt. The mixture was left stirring at rt for 16 hours. GC and $^{19}$F NMR analysis indicated that the reaction was complete. The foil was removed and the reaction mixture was cooled to −15° C. Sodium metabisulfite solution (0.62 eq.) in water (2.35 vol) was added and the biphasic mixture was stirred until the colour of bromine was removed over 30 min. This was filtered to remove precipitated salts and solid slurried in pentane (2×3 vol) and filtered. The combined biphasic mixture was separated and the aqueous layer extracted with pentane (4.4 vol). The combined organics were dried over magnesium sulphate, filtered and concentrated under reduced pressure to give the crude product as a pale yellow oil (Average 93%). The product was purified by distillation at bp 82-88° C. at 1 mmHg to give the desired product (yield 78%). $^1$H NMR (500 MHz, CDCl$_3$) δ: 1.01-1.05 (m, 2H), 1.36-1.41 (m, 2H), 7.33-7.39 (m, 2H), 7.48-7.51 (m, 2H).

8. Dimethyl 2-(4-(1-(trifluoromethyl)cyclopropyl)phenyl)malonate V and 2-(4-(1-(trifluoromethyl)cyclopropyl)phenyl)acetic Acid I 8.1 K$_3$PO$_4$ (3 eq) and toluene (10 vol) were charged in a reactor. After three nitrogen-vacuum cycles, solvent (4.7 vol) was removed by distillation at 110° C. jacket temperature and 250-280 mbar. Note: residual volume in reactor approximately 5 vol. 1-Bromo-4-(1-(trifluoromethyl)cyclopropyl)benzene (1.0 eq.) was added to the reactor at 20° C. Separately, in a round bottom flask, Pd(OAc)$_2$ (0.03 eq), JohnPhos (0.06 eq), and toluene (0.2 vol) was vacuum degassed with nitrogen (applied vacuum to 80-100 mbar until bubbling occurred, followed by pressurization with nitrogen to atmospheric pressure). This suspension was introduced into the reactor with nitrogen pressure. Dimethyl malonate (1.05 eq) was added at 20° C., followed by a rinse of the lines with toluene (0.4 vol). The reactor was vacuum degassed with nitrogen as described above. The mixture was stirred (270 rpm) at reflux at 125-130° C. jacket temperature for 2 h 20 min. In-process control (IPC, approx. 10 mL of reaction mixture withdrawn at 95-100° C.; 20-30 μL thereof was mixed with 1 mL acetonitrile/water 1:1 and filtered) by GC-MS showed >99% conversion. After cooling to 20-30° C., the suspension was filtered over a nutsche equipped with a Teflon cloth. The cake was washed with toluene (2 vol) by application of vacuum. The filtrate (approximately 8 vol) was concentrated at 110° C. jacket temperature and 300 mbar to a residual volume of 1.2-1.6 vol to afford dimethyl 2-(4-(1-(trifluoromethyl)cyclopropyl)phenyl)malonate (V, R$^2$=methyl) as a black solution in toluene that was used as such in the following step. An aliquot was stripped to dryness: 52% w/w solution, the residue solidified to a shiny brown solid. Yield: 96% as a solution in toluene. $^1$H NMR (500 MHz, CDCl$_3$) δ: 1.02-1.07 (m, 2H), 1.35-1.39 (m, 2H), 3.77-3.82 (m, 6H), 4.66-4.69 (m, 1H), 7.38-7.41 (m, 2H), 7.46-7.50 (m, 2H).

8.2 2-(4-(1-(trifluoromethyl)cyclopropyl)phenyl)acetic Acid I

Hydrolysis-decarboxylation

To the solution of dimethyl 2-(4-(1-(trifluoromethyl)cyclopropyl)phenyl)malonate (V, R$^2$=methyl) in toluene (for yield calculation, a 100% yield of the preceding step is assumed) was added water (3.4 vol) and 32% NaOH (1.2 vol). The mixture was heated at reflux at ET 100-105° C. (IT 86° C.) for 2.5 h. IPC (LC-MS) showed complete conversion to the sodium 2-(4-(1-(trifluoromethyl)cyclopropyl)phenyl)malonate (VI). After cooling to 25° C., toluene (0.4 vol) was added and the phase separated. The aqueous phase was circulated through a 3M charcoal cartridge at rt for 30 min. The color changed from a brown-orange to a yellow solution. Water (1 vol) was used for rinse and added to the filtered aqueous phase to the reactor. Toluene (2 vol) was added and solvent (organic: 2 vol, aqueous: 0.4 vol) was removed by distillation at 80-100° C. jacket temperature (IT 80-86° C.) and under reduced pressure (800-900 mbar). Toluene (2 vol) was added and solvent (organic: 2 vol, aqueous: 0.4 vol) was removed by distillation at 80-100° C. jacket temperature and under reduced pressure (800-900 mbar). Toluene (1.2 vol) was added and solvent (organic: 1.2 vol, aqueous: 0.2 vol) was removed by distillation at 80-100° C. jacket temperature and under reduced pressure (600-900 mbar). After cooling to 25° C., the content of the reactor (4.7 vol) was transferred into a feed tank and added to 32% HCl (5.0 eq.) at 80-90° C. during 50 min. The mixture was stirred at 95-100° C. for 2 h 15 min. IPC (LC-MS) showed full conversion. Toluene (2.4 vol) was added to the beige emulsion, cooled to 25° C. for phase separation. The organic phase was washed with water (2.4 vol), filtered through a Whatman Polycap polish filter (approximately 70 μm), and stripped to dryness in a rotavap at 55° C. and reduced pressure (100-8 mbar) to afford the desired product as a light-yellow powder. Yield: 68% over the two steps. 100% a/a by LC-MS. $^1$H NMR assay: 96% w/w. Mp 99.5-100.1° C. $^1$H NMR (500 MHz, CDCl$_3$) δ: 0.99-1.09 (m, 2H), 1.33-1.40 (m, 2H), 3.64-3.71 (m, 2H), 7.27-7.31 (m, 2H), 7.42-7.47 (m, 2H).

9. 2-(4-(1-(trifluoromethyl)cyclopropyl)phenyl)malonic Acid (VII) and 2-(4-(1-(trifluoromethyl)cyclopropyl)phenyl)acetic Acid I

9.1 2-(4-(1-(trifluoromethyl)cyclopropyl)phenyl)malonic Acid VII

In a 5-L double-jacketed flask, a mixture of dimethyl 2-(4-(1-(trifluoromethyl)cyclopropyl)phenyl)malonate (V) (1 eq.), toluene (1 vol), water (3 vol), and 32% NaOH (3.5 eq.) was heated to reflux, 105-100° C. bath temperature. After 70 min at reflux (98% conversion by LC-MS), the mixture was cooled to rt, filtered over a pad of Celite (0.7 wt), and the filter washed with water (2×0.5 vol). The layers were separated. The aqueous phase (pH 14) was washed with toluene (1 vol). In the cleaned reactor, the aqueous phase was set to pH 1-2 by addition of 32% HCl (3.5 eq.) at 20-30° C. The thick, white suspension was cooled to 10° C. and filtered. The cake was washed with water (3×1 vol) and dried at air overnight to afford the desired product as off-white fine water-wet solid. Yield uncorrected for water (106%). 1H NMR (500 MHz, DMSO) δ: 1.09-1.16 (m, 2H), 1.30-1.36 (m, 2H), 4.66-4.73 (m, 1H), 7.26-7.48 (m, 4H), 12.40-13.46 (m, 2H).

9.2
2-(4-(1-(trifluoromethyl)cyclopropyl)phenyl)acetic Acid I 2-(4-(1-(trifluoromethyl)cyclopropyl)phenyl)malonic acid VII (water-wet) was suspended in water (1 vol) and 32% NaOH (0.85 eq.) was added to achieve a clear orange solution after stirring at 25° C. for 15 min. This aqueous phase was washed with toluene (1 vol). The viscous aqueous phase was filtered over a pad of Celite (0.08 wt)/charcoal (0.12 wt)/Celite (0.08 wt), and the cake was washed with water (0.2 vol). The reactor was washed with water and acetone (black-grey precipitation, not soluble in toluene). 24.5% HCl (10 eq.) was heated at reflux (jacket 120° C.) for 40 min to reach the azeotropic steady state of approx. 20% HCl. The basic solution of the sodium salt of 2-(4-(1-(trifluoromethyl)cyclopropyl)phenyl)malonic acid (filtrate above, 4 vol) was added to the refluxing HCl (120° C. oil bath temperature) over 50 min. IPC indicated 67% conversion. The white suspension turned into an emulsion. After stirring at reflux for additional 60 min, a precipitation formed. IPC indicated 99% conversion. The mixture was cooled to 0° C. over 20 min, filtered, the cake was washed with water (6×1 vol), and dried in air for 16 h to afford the desired product as white granular solid. Yield (67%). 100% a/a by LC-MS. >99.5% w/w NMR assay. $^1$H NMR (500 MHz, CDCl$_3$) δ: 0.99-1.09 (m, 2H), 1.33-1.40 (m, 2H), 3.64-3.71 (m, 2H), 7.27-7.31 (m, 2H), 7.42-7.47 (m, 2H).

The invention claimed is:

1. A process, comprising: the reaction of a compound of formula (II)

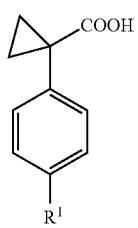

II with SF$_4$ and HF, to give a compound of formula (III)

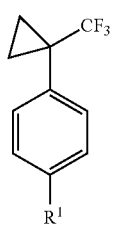

III wherein R$^1$ is H or Br.

2. The process according to claim 1, wherein R$^1$ is H.

3. The process according to claim 1, wherein R$^1$ is Br.

4. The process according to claim 1, wherein dichloromethane is used as a solvent.

5. The process according to claim 1, wherein SF$_4$ is added in an amount of 2 to 10 equivalents.

6. The process according to claim 1, wherein R$^1$ is H and the amount of HF is from 0.4 to 2.5 equivalents.

7. The process according to claim 1, wherein R$^1$ is Br and the amount of HF is from 1.5 to 2.5 equivalents.

8. The process according to claim 1, said process further comprising the reaction of a compound of formula (III)

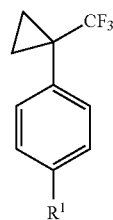

III wherein R$^1$ is Br, with a solvent, K$_3$PO$_4$, Pd(OAc)$_2$, (2-biphenyl)-di-tert-butylphosphine, and

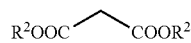

IV to give a compound of formula (V)

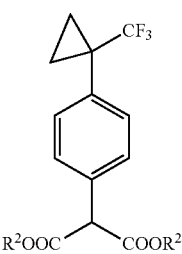

V wherein R$^2$ is methyl, ethyl, isopropyl, n-butyl, or benzyl.

9. The process according to claim 8, wherein R$^2$ is methyl.

10. The process according to claim 1, further comprising converting a compound of formula

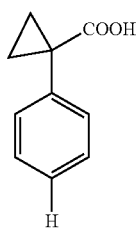 [SMILES: O=C(O)C1(c2ccccc2)CC1]

to a compound of formula

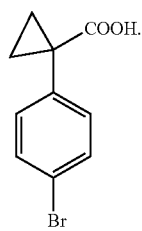 [SMILES: O=C(O)C1(c2ccc(Br)cc2)CC1]

11. The process according to claim 8, further comprising one of the following steps:
   a) treatment of the compound of formula (V), wherein $R^2$ is methyl, ethyl, isopropyl, n-butyl, or benzyl, with NaOH solution, followed by decarboxylation with HCl at 75-100° C.; or
   b) treatment of the compound of formula (V), wherein $R^2$ is methyl, ethyl, isopropyl, n-butyl, or benzyl, with NaOH solution, followed by treatment with HCl at 15-30° C. to obtain an intermediate product of formula (VII)

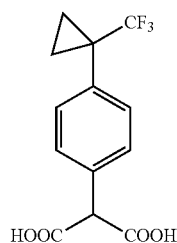

followed by decarboxylation of formula (VII) with HCl at 75-100° C. to obtain the product of formula (I); wherein either step a or b results in the manufacture of the compound of formula (I)

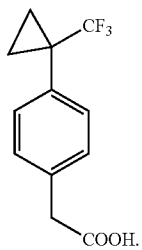

12. A process for the manufacturing of the compound of formula (III)

said process comprising the reaction of a compound of formula (II)

wherein $R^1$ is H or Br, with $SF_4$ and HF.

13. The process according to claim 12, wherein dichloromethane is used as a solvent.

14. The process according to claim 12, wherein $SF_4$ is added in an amount of 2.7 to 10 equivalents.

15. The process according to claim 12, wherein $R^1$ is H, and the amount of HF is from 0.4 to 2.5 equivalents.

16. The process according to claim 12, wherein $R^1$ is Br, and the amount of HF is from 1.5 to 2.5 equivalents.

17. A compound of formula (Va)

wherein each $R^2$ is methyl, ethyl, isopropyl, n-butyl, benzyl or H, or a salt of said compound.

* * * * *